United States Patent [19]

Davies

[11] 4,447,435
[45] * May 8, 1984

[54] 3-METHYLSULFONYLMETHYL-4-QUINOLINONES USEFUL FOR TREATING HYPERTENSION

[75] Inventor: Roy V. Davies, Nottinghamshire, England

[73] Assignee: The Boots Company PLC, Nottingham, England

[*] Notice: The portion of the term of this patent subsequent to Apr. 10, 2001 has been disclaimed.

[21] Appl. No.: 304,165

[22] Filed: Sep. 21, 1981

[30] Foreign Application Priority Data

Sep. 26, 1980 [GB] United Kingdom ............ 8031106
Sep. 26, 1980 [GB] United Kingdom ............ 8031162
Jun. 19, 1981 [GB] United Kingdom ............ 8118879
Jun. 19, 1981 [GB] United Kingdom ............ 8119062

[51] Int. Cl.$^3$ .................. A61K 31/47; C07D 215/22
[52] U.S. Cl. ............................. 424/258; 546/153
[58] Field of Search ........................... 546/153; 424/258

[56] References Cited

U.S. PATENT DOCUMENTS 3,121,725  2/1964  Schnitzer ..................... 546/153 X
3,772,301  11/1973 von Strandtmann et al. ... 424/258 X
4,302,360  11/1981 Davies et al. ................. 424/258
4,343,805  8/1982  Crossley et al. .............. 424/263

FOREIGN PATENT DOCUMENTS 2038825  7/1980  United Kingdom ........... 424/258

OTHER PUBLICATIONS

Van Leusen, et al., J. Org. Chem., vol. 33, No. 1, pp. 66-70, (1968).

Primary Examiner—Donald G. Daus
Assistant Examiner—Diana G. Rivers
Attorney, Agent, or Firm—Gordon W. Hueschen

[57] ABSTRACT

Novel quinolones of the general formula

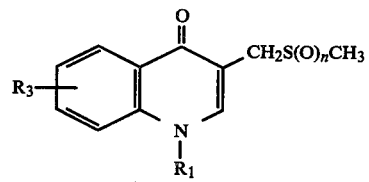

wherein n is 0, 1 or 2; $R_1$ is $C_{1-4}$ alkyl; and $R_3$ is hydrogen, $C_{1-4}$ alkyl, methoxy, methylthio, halo or trifluoromethyl. These compounds have antihypertensive activity and may be used for treating hypertension in mammals.

The quinolones are administered in novel therapeutic compositions comprising a quinolone of the above general formula together with a pharmaceutically acceptable carrier.

Processes for making the novel quinolones are described.

23 Claims, No Drawings

3-METHYLSULFONYLMETHYL-4-QUINOLINONES USEFUL FOR TREATING HYPERTENSION

This invention relates to quinoline compounds with therapeutic activity, to therapeutic compositions containing the quinolones and to processes for preparing the quinolones.

The present invention provides novel quinolones of the general formula I

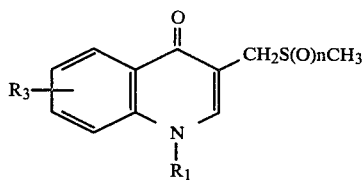

wherein n is 0, 1 or 2; $R_1$ is lower alkyl; and $R_3$ is hydrogen, lower alkyl, methoxy, methylthio, halo or trifluoromethyl.

The term "lower alkyl" denotes a straight or branched chain alkyl radical containing 1-4 carbon atoms, for example methyl, ethyl, propyl, isopropyl, butyl, secondary butyl and tertiary butyl. $R_1$ is preferably methyl. When $R_3$ is halo it is preferably chloro, bromo or fluoro, especially chloro or fluoro.

We have found that the compounds of general formula I have valuable antihypertensive activity. The compounds reduce blood pressure when administered to hypertensive mammals. Thus the present invention also provides therapeutic compositions which comprise a quinolone of general formula I together with a pharmaceutically acceptable carrier.

As used hereinafter, the term "active compound" denotes a quinolone compound of general formula I. In therapeutic use, the active compound may be administered orally, rectally or parenterally, preferably orally. Thus, the therapeutic compositions of the present invention may take the form of any of the known pharmaceutical compositions for oral, rectal or parenteral administration. Pharmaceutically acceptable carriers suitable for use in such compositions are well known in the art of pharmacy. The compositions of the invention suitably contain 0.1-90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compounds are the excipients known in the pharmacists' art. Tablets may be prepared by mixing the active compound with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly capsules, for example hard or soft gelatin capsules, containing the active compound with or without added excipients, may be prepared by conventional means and, if desired, provided with enteric coatings in a known manner. Enteric coated compositions of the invention may be advantageous, depending on the nature of the active compound. The tablets and capsules may conveniently each contain 5-500 mg. of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example, sterile suspension in aqueous and oily media or sterile solutions in a suitable solvent.

In some formulations it may be beneficial to use the compounds of the present invention in the form of particles of very small size, for example, as obtained by fluid energy milling.

In the compositions of the present invention the active compound may, if desired, be associated with other compatible pharmacologically active ingredients.

The therapeutic activity of the compounds of general formula I has been demonstrated by means of tests on standard laboratory animals. Such tests include, for example, the oral administration of compounds to a strain of spontaneously hypertensive rats and the intraduodenal administration of compounds to a strain of normotensive rats.

The compounds of general formula I wherein n is 0 or 2 may be prepared by reacting a compound of general formula II

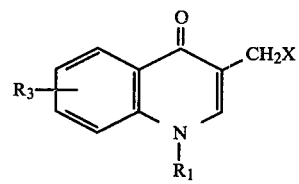

wherein $R_1$ and $R_3$ are as hereinbefore defined and X is a suitable leaving group, for example, chloro or acetoxy, with the methanethiolate anion $CH_3S^\ominus$ or the methanesulphinate anion $CH_3S^\ominus O_2$. Reaction with the methanethiolate anion gives the compounds wherein n is 0 and reaction with the methanesulphinate anion gives the compounds wherein n is 2. Each anion is conveniently provided by means of the appropriate alkali metal salt, for example, the sodium salt. The reaction is effected in a conventional manner for such reactions. The compounds of general formula II are novel and may be prepared by methods known in the art for similar compounds.

The compounds of general formula I wherein n is 1 may be prepared by the oxidation of the corresponding compounds wherein n is 0. Similarly the compounds of general formula I wherein n is 2 may be prepared by the oxidation of the corresponding compounds wherein n is 0 or 1. These oxidations may be effected in a conventional manner for such reactions, for example, using an organic per-acid as the oxidising agent.

The compounds of general formula I wherein n is 2 may also be prepared by hydrolysis of a quinolinium salt of the general formula III

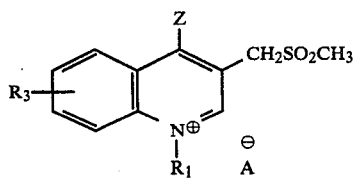

wherein $R_1$ and $R_3$ are as hereinbefore defined, $A^\ominus$ is an anion, and Z is a suitable leaving group, for example, methoxy or chloro. The hydrolysis may be effected by reacting the compound of formula III with water under neutral, acidic or basic conditions, depending upon the nature of the leaving group.

The compounds of the general formula III are novel and may be prepared by alkylation of a quinoline of the general formula IV

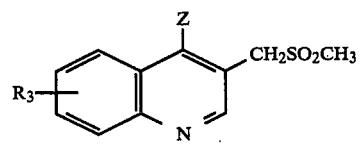

Thus, the anion $A^\ominus$ is conveniently an anion derived from an alkylating agent, for example, a halide or methyl sulphate anion.

The compounds of general formula I wherein n is 2 may also be prepared by thermal rearrangement of a compound of the general formula V

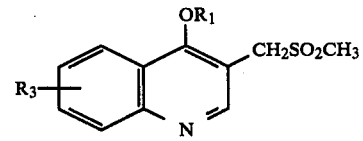

wherein $R_1$ and $R_3$ are as hereinbefore defined. The rearrangement may be effected by heating the compound of general formula V to a temperature above its melting point, optionally in the presence of an inert organic liquid which may be a solvent for the compound V.

The compounds of general formula V are novel. They may be prepared from the corresponding 4-chloro-3-chloromethylquinoline by reaction with sodium methanesulphinate to give the corresponding 4-chloro-3-methylsulphonylmethylquinoline, followed by reaction with sodium alkoxide $NaOR_1$ to give the compound V.

The compounds of general formula I wherein n is 1 or 2 may also be prepared by alkylation of a compound of the general formula VI

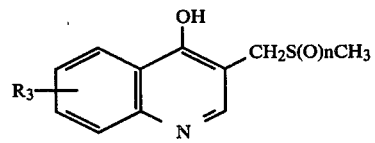

wherein n is 1 or 2 and $R_3$ is as hereinbefore defined. The reaction may be effected by reacting the compound VI with an alkylating agent, for example a dialkyl sulphate or an alkyl iodide, in a conventional manner for such reactions.

The compounds of general formula VI are novel.

The compounds of general formula VI wherein n is 2 may be prepared by reacting a compound of general formula VII

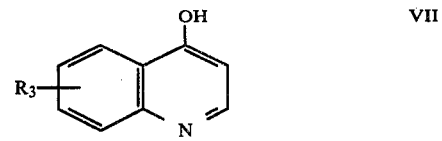

with formaldehyde and sodium methanesulphinate in the presence of a tertiary amine, for example, triethylamine.

The compounds of general formula VI wherein n is 1 may be prepared by the oxidation of the corresponding compounds wherein n is 0. The latter compounds may be prepared by reacting a compound of general formula VII with formaldehyde and sodium methanethiolate in the presence of a tertiary amine, for example, triethylamine.

It will be appreciated by those skilled in the art that, in the compounds of the hereinbefore defined general formula I in which n is 1, the group $CH_3SO-$ contains a chiral centre at the sulphur atom. Thus, such compounds exist in two enantiomeric forms. The present invention includes both enantiomers and the racemic mixture of them.

As mentioned above, the therapeutic activity of the quinolones of general formula I has been demonstrated by tests which include (A) the oral administration of the compounds to a strain of spontaneously hypertensive rat and (B) the intraduodenal administration of the compounds to a strain of normotensive rat. These rats were carried out in the following way:

TEST A

Female rats weight range 180–240 g., of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed round the base of the tail and arterial pulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the pre-dose reading, blood pressure was measured at 1.5 and 5.0 hours after dosing. A compound was designated as active if it gave a reduction of blood pressure of 20% or greater at either of these time intervals.

TEST B

Male normotensive rats (Wistar strain) of weight range 210–240 g. were used. The rats were anesthetised and cannulae placed in a carotid artery and in the duodenum. Blood pressure was recorded electronically by means of a pressure transducer connected to the arterial cannula. The test compound was administered into the duodenum as a solution or suspension in 0.25% aqueous carboxymethylcellulose. Blood pressure was recorded before dosing and for 30 minutes afterwards. Results were obtained as the mean of determinations in three rats per dosage level. Compounds which caused an obvious drug-related fall in blood pressure of 14% or greater during the 30 minute post-dose period were designated as active.

The compounds shown in the following Table I were active in Test A at a dosage of 90 mg./kg. or less and are preferred compounds of the invention.

TABLE 1

[Structure: quinolone with $R_3$ substituent, N-CH$_3$, and $CH_2S(O)_nCH_3$ group]

| Compound | n | $R_3'$ |
| --- | --- | --- |
| 1 | 2 | H |
| 2 | 0 | 7-Cl |
| 3 | 1 | 7-Cl |
| 4 | 2 | 7-Cl |
| 5 | 1 | 7-CF$_3$ |
| 6 | 2 | 7-CF$_3$ |
| 7 | 2 | 7-F |
| 8 | 2 | 6-F |
| 9 | 2 | 7-CH$_3$ |
| 10 | 1 | 7-Br |

The compounds shown in the following Table 2 were not active in Test A at a dosage of 90 mg./kg. but were active in Test B at a dosage of 90 mg./kg.

TABLE 2

[Structure: quinolone with $R_3$ substituent, N-$R_1$, and $CH_2S(O)_nCH_3$ group]

| Compound | $R_1$ | n | $R_3$ |
| --- | --- | --- | --- |
| 11 | CH$_3$ | 2 | 8-OCH$_3$ |
| 12 | CH$_3$ | 1 | 6-F |
| 13 | CH$_3$ | 2 | 7-SCH$_3$ |
| 14 | CH$_3$ | 1 | 7-C$_2$H$_5$ |
| 15 | CH$_3$ | 2 | 7-C$_2$H$_5$ |
| 16 | CH$_3$ | 1 | 8-Cl |
| 17 | CH$_3$ | 0 | 7-Br |
| 18 | CH$_3$ | 2 | 7-Br |
| 19 | CH$_3$ | 2 | 7-t-C$_4$H$_9$ |
| 20 | C$_2$H$_5$ | 2 | H |
| 21 | CH$_3$ | 0 | H |
| 22 | CH$_3$ | 1 | H |
| 23 | CH$_3$ | 0 | 7-CF$_3$ |
| 24 | CH$_3$ | 0 | 6-OCH$_3$ |
| 25 | CH$_3$ | 2 | 6-OCH$_3$ |
| 26 | CH$_3$ | 0 | 7-OCH$_3$ |
| 27 | CH$_3$ | 1 | 7-OCH$_3$ |
| 28 | CH$_3$ | 2 | 7-OCH$_3$ |
| 29 | CH$_3$ | 0 | 8-OCH$_3$ |
| 30 | CH$_3$ | 1 | 8-OCH$_3$ |
| 31 | CH$_3$ | 0 | 7-F |
| 32 | CH$_3$ | 1 | 7-F |
| 33 | CH$_3$ | 1 | 8-F |
| 34 | CH$_3$ | 2 | 8-F |
| 35 | CH$_3$ | 0 | 6-CH$_3$ |
| 36 | CH$_3$ | 1 | 6-CH$_3$ |
| 37 | CH$_3$ | 2 | 6-CH$_3$ |
| 38 | CH$_3$ | 2 | 8-CH$_3$ |

TABLE 2-continued

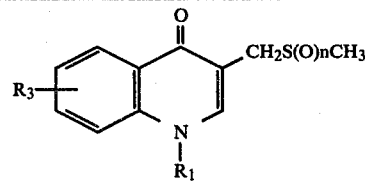

| Compound | $R_1$ | n | $R_3$ |
| --- | --- | --- | --- |
| 39 | CH$_3$ | 0 | 6-Cl |
| 40 | CH$_3$ | 1 | 6-Cl |
| 41 | CH$_3$ | 2 | 6-Cl |
| 42 | CH$_3$ | 0 | 8-Cl |
| 43 | CH$_3$ | 2 | 8-Cl |
| 44 | CH$_3$ | 0 | 7-t-C$_4$H$_9$ |
| 45 | CH$_3$ | 1 | 7-t-C$_4$H$_9$ |
| 46 | n-C$_3$H$_7$ | 2 | H |

Compounds 11–20 inclusive were particularly active in Test B and are the preferred compounds of those in Table 2.

The present invention provides a method of reducing blood pressure in a hypertensive mammal which comprises the administration of a quinolone compound of the hereinbefore defined general formula I. Administration may be enteral or parenteral; enteral administration, especially oral administration, is preferred. A suitable dosage for treating hypertensive in mammals, including man, is generally within the range 0.1–100 mg./kg./day, more usually 0.5–75 mg./kg./day and especially 1–50 mg./kg./day, given in single or divided doses. Unit dosage forms suitably contain 1–500 mg., especially 5–500 mg., of the active compound.

Many of the compounds of the general formula I have an unexpected superior antihypertensive activity to that of structurally related compounds. For example, the compounds in Table 1 are active when orally administered to rats at a dosage of 90 mg./kg., whereas other structurally related compounds are not active in this test. Certain compounds of the general formula I, for example compounds 1, 4 and 6 in Table 1, are characterized by a substantial and unexpected superior antihypertensive activity to that of certain known structurally related compounds.

It will be appreciated by those skilled in the art that the compounds of general formula I wherein n is 0 are intermediates one step removed from the corresponding compounds wherein n is 1 or 2. Similarly the compounds of general formula I wherein n is 1 are intermediates one step removed from the corresponding compounds wherein n is 2.

The invention is illustrated by the following non-limitative Examples, in which parts and percentages are by weight and compositions of mixed solvents are given by volume. Novel compounds were characterised by one or more of the following spectroscopic techniques: nuclear magnetic resonance (H$^1$ or C$^{13}$), infra red and mass spectroscopy. Additionally, the products of the Examples had satisfactory elemental analyses. Melting points are given in degrees centigrade.

EXAMPLE 1

(a) A solution of thionyl chloride (9.48 g.) in dichloromethane (800 ml.) was added during 4 hours to a refluxing suspension of finely ground 3-hydroxymethyl-1-methyl-4-quinolone (15.01 g.) in dichloromethane (200 ml.). The mixture was boiled under reflux for a further 1.5 hours, cooled to room temperature and filtered to give the novel compound 3-chloromethyl-1-methyl-4-quinolone hydrochloride m.p. 178°–181°. The compound (12.71 g.) was added to a stirred solution of sodium methanethiolate in methanol at 0° (116 ml. containing 0.109 mole NaSCH₃) during 5 minutes. The resulting mixture was allowed to warm to room temperature and kept overnight. The mixture was cooled to 0° and water added to form a solution. The solution was neutralised to pH 7.0 with dilute hydrochloric acid and filtered. Methanol was distilled from the filtrate and the residue extracted with dichloromethane (3×50 ml.). The combined extracts were dried over anhydrous magnesium sulphate and evaporated to give a solid product. The product was purified by high pressure liquid chromatography over silica gel, eluting with isopropanol:dichloromethane 15:85 at a flow rate of 300 ml. per minute. The same solvent was used for applying the product to the silica gel. This procedure gave the novel 1-methyl-3-methylthiomethyl-4-quinolone m.p. 118°–120°.

(b) To a solution of the above 1-methyl-3-methylthiomethyl-4-quinolone (4.86 g.) in dichloromethane (220 ml.) at −20° was added a solution of 3-chloroperbenzoic acid (85%, 4.86 g.) in dichloromethane (220 ml.) during 1 hour. The solution was allowed to warm to room temperature and extracted with saturated aqueous sodium bicarbonate until free of per-acid. The organic phase was dried over anhydrous magnesium sulphate and evaporated to give a solid product. The product was crystallized from acetone to give the novel 1-methyl-3-methylsulphinylmethyl-4-quinolone, m.p. 93°–95°.

EXAMPLE 2

To a stirred solution of 1-methyl-3-methylthiomethyl-4-quinolone (1.3 g.) in dichloromethane (60 ml.) at −20° was added a solution of 3-chloroperbenzoic acid (85%, 2.75 g.) in dichloromethane (85 ml.) during 20 minutes. The stirred solution was allowed to warm to room temperature and then stirred for a further period of 1 hour. The solution was extracted with saturated aqueous sodium bicarbonate until free of per-acid. The organic phase was dried over anhydrous magnesium sulphate and evaporated to give a solid product. This was crystallised from acetone to give the novel 1-methyl-3-methylsulphonylmethyl-4-quinolone, m.p. 203°–205°.

EXAMPLE 3

(a) 3-Chloromethyl-1-methyl-7-trifluoromethyl-4-quinolone hydrochloride (4.7 g.) was added to a stirred solution of sodium methanethiolate in methanol (16 ml. containing 0.039 mole NaSMe) at 0° during 5 minutes. The resulting mixture was allowed to warm to room temperature then poured into water (100 ml.). The resulting precipitate was collected, dried and crystallized from dichloromethane:petroleum ether (b.p. 60°–80°) to give the novel 1-methyl-3-methylthiomethyl-7-trifluoromethyl-4-quinolone, m.p. 182°–184°.

(b) The starting material for the above preparation was prepared as follows:

A mixture of 4-hydroxy-7-trifluoromethylquinoline (30.0 g.), 40% aqueous formaldehyde solution (36 ml.) and 1 M aqueous solution hydroxide solution (250 ml.) was stirred at 40°–50° for 8 hours. The solid product was collected and dried to give the novel 4-hydroxy-3-hydroxymethyl-7-trifluoromethylquinoline, m.p. 302–304°.

Dimethyl sulphate (24.4 g.) was added over 5 minutes to a stirring solution of 4-hydroxy-3-hydroxymethyl-7-trifluoromethylquinoline (23.6 g.) and potassium hydroxide (16.3 g.) in a mixture of water (50 ml.) and tetrahydrofuran (50 ml.) at room temperature. After stirring for a further 3 hours at this temperature the solid product was collected. The filtrate was extracted with dichloromethane (3×200 ml.). The combined extracts were dried over anhydrous magnesium sulphate and evaporated to give a second crop of the solid. The combined solids were purified by high pressure liquid chromatography over silica gel, eluting with isopropanol: dichloromethane 10:90 at a flow rate of 200 ml. per minute. The same solvent was used for applying the product to silica gel. This procedure gave the novel 3-hydroxymethyl-1-methyl-7-trifluoromethyl-4-quinolone, m.p. 172°–175°.

A solution of thionyl chloride (2.32 g.) in dichloromethane (100 ml.) was added during 1.5 hours to a refluxing suspension of finely ground 3-hydroxymethyl-1-methyl-7-trifluoromethyl-4-quinolone (5.0 g.) in dichloromethane (200 ml.). The solution was boiled under reflux for a further 0.5 hours then evaporated to dryness under reduced pressure to give the novel 3-chloromethyl-1-methyl-7-trifluoromethyl-4-quinolone hydrochloride, m.p. 182°–189°.

EXAMPLE 4

To a stirred solution of 1-methyl-3-methylthiomethyl-7-trifluoromethyl-4-quinolone (6.5 g.) in dichloromethane (150 ml.) at −10° was added a solution of 3-chloroperbenzoic acid (85%, 4.2 g.) in dichloromethane (90 ml.) during 30 minutes. The solution was extracted with saturated aqueous sodium bicarbonate until free of per-acid. The organic phase was dried over anhydrous magnesium sulphate and evaporated to give a solid product. This was crystallised from ethyl acetate:dichloromethane to give the novel 1-methyl-3-methylsulphinylmethyl-7-trifluoromethyl-4-quinolone, m.p. 208°–210°.

EXAMPLE 5

To a stirred solution of 1-methyl-3-methylthiomethyl-7-trifluoromethyl-4-quinolone (7.8 g.) in dichloromethane (150 ml.) at room temperature was added a solution of 3-chloroperbenzoic acid (85%, 11.3 g.) in dichloromethane (100 ml.) during 3 minutes. After stirring at this temperature for a further period of 1 hour the solution was extracted with saturated aqueous sodium bicarbonate until free of per-acid. The organic phase was dried over anhydrous magnesium sulphate and evaporated to give a solid product. This was crystallised from industrial methylated spirit: dichloromethane to give the novel 1-methyl-3-methylsulphonylmethyl-7-trifluoromethyl-4-quinolone, m.p. 240°–242°.

EXAMPLE 6

In a similar manner to that described in Example 3 7-chloro-4-hydroxy-3-hydroxymethylquinoline was treated with dimethyl sulphate to give the novel 7-chloro-1-methyl-3-hydroxymethyl-4-quinolone, m.p. 204°–206° (from industrial methylated spirit). Reaction of this product with thionyl chloride gave 7-chloro-3-chloromethyl-1-methyl-4-quinolone hydrochloride, m.p. 205°–207°, which was reacted with sodium methanethiolate to give the novel 7-chloro-1-methyl-3-methylthiomethyl-4-quinolone, m.p. 163°–164° (from industrial methylated spirit).

EXAMPLE 7

In a similar manner to that described in Example 4 7-chloro-1-methyl-3-methylthiomethyl-4-quinolone was oxidised with 3-chloroperbenzoic acid to give the novel 7-chloro-1-methyl-3-methylsulphinylmethyl-4-quinolone m.p. 180°–181° (from dichloromethane:petroleum ether (b.p. 60°–80°).

EXAMPLE 8

In a similar manner to that described in Example 5 7-chloro-1-methyl-3-methylthiomethyl-4-quinolone was oxidised with 3-chloroperbenzoic acid to give the novel 7-chloro-1-methyl-3-methylsulphonylmethyl-4-quinolone, m.p. 215°–216° (from ethanol).

EXAMPLE 9

(a) In a similar manner to that described in Example 5 6-fluoro-1-methyl-3-methylthiomethyl-4-quinolone was oxidised with 3-chloroperbenzoic acid to give the novel 6-fluoro-1-methyl-3-methylsulphonylmethyl-4-quinolone, m.p. 200°–205° (from industrial methylated spirit).

(b) The starting material for the above preparation was prepared in a similar manner to that described in Example 3.

6-Fluoro-4-hydroxyquinoline was reacted with 40% aqueous formaldehyde in aqueous sodium hydroxide solution to give the novel 6-fluoro-4-hydroxy-3-hydroxymethylquinoline m.p. 310°–315°. The product was methylated with dimethyl sulphate to give the novel 6-fluoro-1-methyl-3-hydroxymethyl-4-quinolone, m.p. 209°–212°. Reaction of this product with thionyl chloride, then sodium methanethiolate gave the novel 6-fluoro-1-methyl-3-methylthiomethyl-4-quinolone, m.p. 114°–116° (from industrial methylated spirit).

(c) This sulphide was oxidised with a molar amount of 3-chloroperbenzoic acid in dichloromethane at −20° to −30° in a similar way to that described in Example 4 to give the corresponding novel sulphoxide 6-fluoro-1-methyl-3-methylsulphinylmethyl-4-quinolone, m.p. 154°–156° (from industrial methylated spirit).

EXAMPLE 10

(a) A mixture of 7-fluoro-4-hydroxyquinoline (91.5 g., containing some 5-fluoro isomer), aqueous sodium hydroxide (1.0 N, 666 ml.) and aqueous formaldehyde (37%, 91.5 ml.) was stirred at 35°–37° for 5.5 hours. A further portion of aqueous formaldehyde (37%, 91.5 ml.) was added and stirring continued for 64 hours. The solid product was collected by filtration, added to water (600 ml.) and the mixture acidified to pH 4.0 with concentrated hydrochloric acid. The solid residue was collected, washed with water and dried to give the novel 7-fluoro-4-hydroxy-3-hydroxymethylquinoline, m.p. 295°–300° (containing some 5-fluoro isomer). Further product m.p. 295°–300°, was obtained from the alkaline filtrate of the reaction mixture by acidification to pH 4.0 with concentrated hydrochloric acid, and was combined with the first product.

(b) This combined product was mixed with water (1300 ml.), potassium hydroxide (17.3 g.) and dimethyl sulphate (35 ml.). The mixture was stirred at 25° for 17 hours and then basified with 5 N aqueous potassium hydroxide. The residue was collected, washed with water, dried and crystallised from industrial methylated spirit to give the novel compound 7-fluoro-3-hydroxymethyl-1-methyl-4-quinolone, m.p. 219°–222°.

(c) This compound was reacted with thionyl chloride in a similar way to that described in Example 3 to give 3-chloromethyl-7-fluoro-1-methyl-4-quinolone, m.p. 169°–171°.

(d) This compound (20.7 g.) was added during 10 minutes to a stirred solution of sodium methanethiolate in methanol [from methanethiol (10 ml.) and methanolic sodium methoxide (0.64 M, 280 ml.)] at 10°. The mixture was stirred at 20° for 1 hour, then poured into water (700 ml.). The precipitate was collected and crystallised from industrial methylated spirit to give the novel compound 7-fluoro-1-methyl-3-methylthiomethyl-4-quinolone, m.p. 167°–169°.

(e) This sulphide was oxidised with an equimolar amount of 3-chloroperbenzoic acid in a similar way to that described in Example 1 to give the corresponding novel sulphoxide, 7-fluoro-1-methyl-3-methylsulphinylmethyl-4-quinolone, m.p. 179°–180° (from industrial methylated spirit).

(f) The sulphide from (d) was oxidised with 2 molar equivs. of 3-chloroperbenzoic acid in a similar way to that described in Example 2 to give the corresponding novel sulphone 7-fluoro-1-methyl-3-methylsulphonylmethyl-4-quinolone, m.p. 212°–215° (from industrial methylated spirit).

EXAMPLE 11

(a) To a soluttion of 7-methyl-4-hydroxyquinoline (2.63 g.) in water (55 ml.) were added aqueous formaldehyde (37%, 3.5 ml.), sodium methanesulphinate (6.39 g.) and triethylamine (4 ml.). The mixture was heated with stirring on the steam bath for 60 hours, cooled to room temperature, and filtered. The solid residue was washed with water and dried to give the novel compound 4-hydroxy-7-methyl-3-methylsulphonylmethylquinoline, m.p. 285°–290°.

(b) This product (3.0 g.) was dissolved in aqueous potassium hydroxide (22 ml., containing 1.91 g. KOH). Dimethyl sulphate (1.7 ml.) was added and the mixture stirred for 16 hours at room temperature. The precipitated solid was collected by filtration, washed with water, dried and crystallised from industrial methylated spirit. The product was washed with diethyl ether to give the novel compound 1,7-dimethyl-3-methylsulphonylmethyl-4-quinolone, m.p. 193°–195°.

EXAMPLE 12

In a similar way to that described in Example 10, the following reactions were carried out.

(a) 4-Hydroxy-6-methoxyquinoline was reacted with formaldehyde in aqueous sodium hydroxide (initially at 40°–50°, then kept at 60° for 18 hours) to give the novel compound 4-hydroxy-3-hydroxymethyl-6-methoxyquinoline, m.p. 327°–334°.

(b) This compound (1.64 g.) was mixed with 2-butanone (80 ml.), anhydrous potassium carbonate (2.2 g.) and dimethyl sulphate (1.01 g.) and the mixture was boiled under reflux for 3 hours. The hot mixture was filtered. The filtrate was cooled to give the novel compound 3-hydroxymethyl-6-methoxy-1-methyl-4-quinolone, m.p. 194°–197°.

(c) This compound was reacted with thionyl chloride in dichloromethane to give the novel compound 3-chloromethyl-6-methoxy-1-methyl-4-quinolone hydrochloride, m.p. 204°–206° (dec.).

(d) This compound in finely ground form (10.0 g.) was added portionwise to stirred solution of sodium methanethiolate in methanol (60 ml. containing 0.12 M NaSCH₃) at 0°–5°. The mixture was then stirred at room temperature for 1 hour and poured into ice/water. The precipitate was filtered off and the filtrate was extracted four times with dichloromethane. The combined extract was dried and evaporated. The residue was crystallised from isopropanol to give the novel compound 6-methoxy-1-methyl-3-methylthiomethyl-4-quinolone, m.p. 122°–123°.

(e) This sulphide was oxidised with 2 molar equivs. of 3-chloroperbenzoic acid in dichloromethane to give the novel compound 6-methoxy-1-methyl-3-methylsulphonylmethyl-4-quinolone, m.p. 264°–267° (from 2-ethoxyethanol).

EXAMPLE 13

In a similar way to that described in Example 12, the following reactions was carried out.

(a) 4-Hydroxy-7-methoxyquinoline was reacted with formaldehyde in aqueous sodium hydroxide (initially at 40°–50°, then kept at 60° for 18 hours) to give the novel compound 4-hydroxy-3-hydroxymethyl-7-methoxyquinoline, m.p. 291°–297°.

(b) This compound was methylated with dimethyl sulphate in aqueous potassium hydroxide at 5°–10° to give the novel compound 3-hydroxymethyl-7-methoxy-1-methyl-4-quinolone, m.p. 164°–166° (from industrial methylated spirit).

(c) This compound was reacted with thionyl chloride in dichloromethane to give the novel compound 3-chloromethyl-7-methoxy-1-methyl-4-quinolone hydrochloride, m.p. 198°–200° (dec.).

(d) This compound in finely ground form was reacted with sodium methanethiolate in methanol at 0°–5°. The reaction mixture at room temperature was poured into ice/water. The precipitate was filtered off and the filtrate extracted four times with dichloromethane. The combined extract was dried and evaporated. The residue was purified by high pressure liquid chromatography over silica gel, eluting with dichloromethane:isopropanol 95:5 at a flow rate of 250 ml. per minute.

This procedure gave the novel compound 7-methoxy-1-methyl-3-methylthiomethyl-4-quinolone, m.p. 135°–136°.

(e) This sulphide was oxidised with an equimolar amount 3-chloroperbenzoic acid in dichloromethane to give the corresponding sulphoxide as an impure product. The product was purified by high pressure liquid chromatography over silica gel, using dichloromethane:industrial methylated spirit 90:10 as the eluant at a flow rate of 200 ml. per minute to give the novel sulphoxide 7-methoxy-1-methyl-3-methylsulphinylmethyl-4-quinolone, m.p. 171°–174°.

(f) The sulphide from (d) was oxidised with 2 molar equivs. of 3-chloroperbenzoic acid in dichloromethane to give the novel sulphone 7-methoxy-1-methyl-3-methylsulphonylmethyl-4-quinolone, m.p. 248°–249° (from 2-ethoxyethanol).

EXAMPLE 14

In a similar way to that described in Example 10, the following reactions were carried out.

(a) 4-Hydroxy-8-methoxyquinoline was reacted with formaldehyde in aqueous sodium hydroxide to give the novel compound 4-hydroxy-3-hydroxymethyl-8-methoxyquinoline, m.p. >350°.

(b) This compound was methylated with dimethyl sulphate in aqueous potassium hydroxide at 10° to give the novel compound 3-hydroxymethyl-1-methyl-8-methoxy-4-quinolone, m.p. 162°–167°.

(c) This compound was reacted with thionyl chloride in dichloromethane to give the novel compound 3-chloromethyl-8-methoxy-1-methyl-4-quinolone hydrochloride, m.p. 184°–186° (dec.).

(d) This compound was reacted with sodium methanethiolate in methanol at 0°–5° to give the novel compound 8-methoxy-1-methyl-3-methylthiomethyl-4-quinolone, m.p. 143°–145°.

(e) This sulphide was oxidised with an equimolar amount of 3-chloroperbenzoic acid in dichloromethane to give the corresponding novel sulphoxide 8-methoxy-1-methyl-3-methylsulphinylmethyl-4-quinolone, m.p. 162°–164° (crystallised from ethyl acetate and then ethyl acetate:dichloromethane 10:4).

(f) The sulphide from (d) was oxidised with 2 molar equivs. of 3-chloroperbenzoic acid in dichloromethane to give the corresponding novel sulphone 8-methoxy-1-methyl-3-methylsulphonylmethyl-4-quinolone, m.p. 193°–195° (from industrial methylated spirit).

EXAMPLE 15

In a similar way to that described in Example 10, the following reactions were carried out.

(a) 8-Fluoro-4-hydroxyquinoline was reacted with formaldehyde in aqueous sodium hydroxide to give the novel compound 8-fluoro-4-hydroxy-3-hydroxymethylquinoline, m.p. 176°–178° (from dichloromethane).

(b) This compound was methylated with dimethyl sulphate in aqueous potassium hydroxide at 20° to give the novel compound 8-fluoro-3-hydroxymethyl-1-methyl-4-quinolone, m.p. 206°–210°.

(c) This compound was reacted with thionyl chloride in dichloromethane to give the novel compound 3-chloromethyl-8-fluoro-1-methyl-4-quinolone, 0.1 HCl m.p. 230°–233°.

(d) This compound was reacted with sodium methanethiolate in methanol at 0° to give the novel compound 8-fluoro-1-methyl-3-methylthiomethyl-4-quinolone, m.p. 165°–167° (from industrial methylated spirit).

(e) This sulphide was oxidised with an equimolar amount of 3-chloroperbenzoic acid in dichloromethane to give the corresponding novel sulphoxide 8-fluoro-1-methyl-3-methylsulphinylmethyl-4-quinolone, m.p. 170°–172° (from industrial methylated spirit).

(f) The sulphide from (d) was oxidised with 2 molar equivs. of 3-chloroperbenzoic acid in dichloromethane to give the corresponding novel sulphone 8-fluoro-1-methyl-3-methylsulphonylmethyl-4-quinolone, m.p. 236°–238°.

EXAMPLE 16

(a) A mixture of 4-hydroxy-7-methylthioquinoline (4.2 g.), sodium methanesulphinate (8.2 g.), aqueous formaldehyde (37%, 9.0 ml.), triethylamine (2.85 ml.), industrial methylated spirit (130 ml.) and water (50 ml.) was stirred and boiled under reflux for 96 hours. The mixture was cooled to room temperature and filtered. The residue was washed with hot industrial methylated spirit to give the novel compound 4-hydroxy-3-methylsulphonylmethyl-7-methylthioquinoline, m.p. 290°–292°.

(b) This compound was methylated with dimethyl sulphate in aqueous tetrahydrofuran (50% v/v) at 20° to give the novel compound 1-methyl-3-methylsulphonylmethyl-7-methylthio-4-quinolone, m.p. 243°–245° (from industrial methylated spirit).

EXAMPLE 17

In a similar way to that described in Example 10, the following reactions were carried out.

(a) 4-Hydroxy-6-methylquinoline was reacted with formaldehyde in aqueous sodium hydroxide at 40°–45° for 60 hours to give the novel compound 4-hydroxy-3-hydroxymethyl-6-methylquinoline, m.p. 188°–189° (dec.).

(b) This compound was methylated with dimethyl sulphate in aqueous potassium hydroxide at room temperature to give the novel compound 3-hydroxymethyl-1,6-dimethyl-4-quinolone, m.p. 171°–173° (from industrial methylated spirit:ethyl acetate).

(c) This compound was reacted with thionyl chloride in dichloromethane to give the novel compound 3-chloromethyl-1,6-dimethyl-4-quinolone hydrochloride, m.p. 215°–224°.

(d) This compound was reacted with sodium methanethiolate in methanol at 0°–5°. The reaction mixture was poured into water, the solid boiled with industrial methylated spirit, cooled and filtered. The filtrate was concentrated to give the novel 1,6-dimethyl-3-methylthiomethyl-4-quinolone, m.p. 142°–143°.

(e) Oxidation of this sulphide with an equimolar amount of 3-chloroperbenzoic acid gave the corresponding novel sulphoxide 1,6-dimethyl-3-methylsulphinylmethyl-4quinolone, m.p. 177°–179° (from ethyl acetate).

(f) Oxidation of the sulphide from (d) with 2 molar equivs. of 3-chloroperbenzoic acid gave the corresponding novel sulphone 1,6-dimethyl-3-methylsulphonylmethyl-4-quinolone, m.p. 252°–255° (from industrial methylated spirit).

EXAMPLE 18

(a) To a stirred suspension of 4-hydroxy-8-methylquinoline (10.0 g.) in triethylamine (8.8 ml.) and industrial methylated spirit (15 ml.) at 0°–5° was added methanethiol (10.4 ml.) followed by aqueous formaldehyde (40%, 14.2 ml.). The mixture was stirred and boiled under reflux for 30 hours. Aqueous formaldehyde (40%, 14.2 ml.) was added dropwise to a stirred solution of triethylamine (8.8 ml.) and methanethiol (10.4 ml.) in ethanol (15 ml.) maintaining the temperature below 10°. The resulting solution was added to the above reaction mixture and the mixture was stirred and boiled under reflux for 20 hours. The mixture was left to cool overnight. The resulting crystalline solid was collected by filtration to give the novel compound 4-hydroxy-8-methyl-3-methylthiomethylquinoline, m.p. 226°–228°.

(b) To a stirred solution of this compound (2.0 g.) in dichloromethane (80 ml.) was added dropwise a solution of 85% 3-chloroperbenzoic acid (4.0 g.) in dichloromethane (100 ml.). The solid precipitate was collected by filtration, washed with diethyl ether and dried to give the novel compound 4-hydroxy-8-methyl-3-methylsulphonylmethylquinoline, m.p. 274°–276° (dec.).

(c) To a suspension of this sulphone (1.92 g.) and potassium carbonate (2.11 g.) in 2-butanone (100 ml.) was added dimethyl sulphate (1.08 ml.). The mixture was boiled under reflux for 16 hours and filtered while hot. The filtrate was allowed to cool to give the novel crystalline product 1,8-dimethyl-3-methylsulphonylmethyl-4-quinolone, m.p. 244°–246°.

EXAMPLE 19

(a) The novel intermediate 7-ethyl-4-hydroxyquinoline was prepared as follows.

A mixture of 3-ethylaniline (121 g.) and diethyl ethoxymethylenemalonate (230 g.) was stirred on a steam bath at 95°–100° for 1 hour, when evolution of ethyl alcohol had ceased. The mixture was cooled to −60° and the solid mass triturated with petroleum ether (b.p. 40°–60°). The liquors were decanted from the solid product and on warming to room temperature the novel diethyl (3-ethylanilino) methylenemalonate was obtained as an oil.

A solution of this oil (50 g.) in diphenyl ether (90 ml.) at 60°–80° was added during 30 minutes to refluxing diphenyl ether (420 ml.). The mixture was refluxed for a further 30 minutes then allowed to cool to room temperature. The mixture was diluted with an equal volume of petroleum ether (b.p. 60°–80°) and the tan solid collected, washed with more petroleum ether, and dried to give the novel ethyl 7-ethyl-4-hydroxyquinoline-3-carboxylate, m.p. 257°–260°.

A stirred mixture of ethyl 7-ethyl-4-hydroxyquinoline-3-carboxylate and 5 M aqueous sodium hydroxide solution was heated to reflux. When all the solids had dissolved the solution was boiled for a further 30 minutes, cooled, and acidified to pH 4.0 with glacial acetic acid (30 ml.). The solid was collected, washed with water until the washings were neutral, and dried to give the novel compound 7-ethyl-4-hydroxyquinoline-3-carboxylic acid, m.p. 175°–178°.

7-Ethyl-4-hydroxyquinoline-3-carboxylic acid (200.8 g.) was added portionwise during 70 minutes to boiling diphenyl ether (1.64 liters). The stirring mixture was cooled to room temperature and an equal volume of petroleum ether (b.p. 60°–80°) added. The brown solid was collected and crystallised from water to give the novel 7-ethyl-4-hydroxyquinoline m.p. 148°–152°.

In a similar way to that described in Example 10, the following reactions were carried out.

(b) 7-Ethyl-4-hydroxyquinoline was reacted with 40% aqueous formaldehyde in aqueous sodium hydroxide to give the novel compound 7-ethyl-4-hydroxy-3-hydroxymethylquinoline, m.p. 180°–182°.

(c) This compound was methylated with dimethyl sulphate to give the novel compound 7-ethyl-1-methyl-3-hydroxymethyl-4-quinolone, m.p. 147°–148.5° (from ethyl acetate).

(d) This compound was reacted with thionyl chloride to give 3-chloromethyl-7-ethyl-1-methyl-4-quinolone, m.p. 136.5°–148° (dec.).

(e) This compound was reacted with sodium methanethiolate to give the novel compound 7-ethyl-1-methyl-3-methylthiomethyl-4-quinolone, m.p. 104°–106° (from industrial methylated spirit).

(f) This sulphide was oxidised with an equimolar amount of 3-chloroperbenzoic acid to give the novel sulphoxide 7-ethyl-1-methyl-3-methylsulphinylmethyl-4-quinolone, m.p. 144°–146° (from ethyl acetate).

(g) The sulphide from (e) was oxidised with 2 molar equivs. of 3-chloroperbenzoic acid to give the novel sulphone 7-ethyl-1-methyl-3-methylsulphonylmethyl-4-quinolone, m.p. 172°–174° (from industrial methylated spirit).

EXAMPLE 20

In a similar way to that described in Example 10, the following reactions were carried out.

(a) 6-Chloro-4-hydroxyquinoline was reacted with formaldehyde in aqueous sodium hydroxide at 55° for 24 hours to give the novel compound 6-chloro-4-hydroxy-3-hydroxymethylquinoline, m.p.>300°.

(b) This compound was methylated with dimethyl sulphate in aqueous potassium hydroxide at room temperature to give the novel compound 6-chloro-3-hydroxymethyl-1-methyl-4-quinolone, m.p. 207°–209° (from industrial methylated spirit/water).

(c) This compound was reacted with thionyl chloride to give the novel compound 6-chloro-3-chloromethyl-1-methyl-4-quinolone hydrochloride.

(d) This compound was reacted with sodium methanethiolate in methanol to give a crude product which was purified by high pressure liquid chromatography over silica gel, eluting with dichloromethane:isopropanol 90:10 at a flow rate of 250 ml. per minute. There was obtained the novel compound 6-chloro-1-methyl-3-methylthiomethyl-4-quinolone, m.p. 148°–150°.

(e) This sulphide was oxidised with an equimolar amount of 3-chloroperbenzoic acid to give the novel sulphoxide 6-chloro-1-methyl-3-methylsulphinylmethyl-4-quinolone, m.p. 217°–219°.

(f) The sulphide from (d) was oxidised with 2 molar equivs. of 3-chloroperbenzoic acid to give the novel sulphone 6-chloro-1-methyl-3-methylsulphonylmethyl-4-quinolone, m.p. 237°–239° (from ethyl acetate).

EXAMPLE 21

In a similar way to that described in Example 10, the following reactions were carried out.

(a) 8-Chloro-4-hydroxyquinoline was reacted with formaldehyde in aqueous sodium hydroxide to give the novel compound 8-chloro-4-hydroxy-3-hydroxymethylquinoline, m.p.>300° (from methanol).

(b) This compound was methylated by boiling under reflux with dimethyl sulphate and potassium carbonate in 2-butanone. There was obtained the novel compound 8-chloro-3-hydroxymethyl-1-methyl-4-quinolone, m.p. 182°–184° (from methanol/water).

(c) This compound was reacted with thionyl chloride in dichloromethane to give the novel compound 8-chloro-3-chloromethyl-1-methyl-4-quinolone hydrochloride.

(d) This compound was reacted with sodium methanethiolate in methanol to give the novel compound 8-chloro-1-methyl-3-methylthiomethyl-4-quinolone, m.p. 146°–148° (from ethyl acetate).

(e) This sulphide was oxidised with an equimolar amount of 3-chloroperbenzoic acid to give the novel sulphoxide 8-chloro-1-methyl-3-methylsulphinylmethyl-4-quinolone, m.p. 156°–158° (from ethyl acetate).

(f) The sulphide from (d) was oxidised with 2 molar equivs. of 3-chloroperbenzoic acid to give the novel sulphone 8-chloro-1-methyl-3-methylsulphonylmethyl-4-quinolone, m.p. 225°–227° (from industrial methylated spirit).

EXAMPLE 22

In a similar way to that described in Example 10, the following reactions were carried out.

(a) 7-Bromo-4-hydroxyquinoline was reacted with formaldehyde in aqueous sodium hydroxide to give the novel compound 7-bromo-4-hydroxy-3-hydroxymethylquinoline, m.p. >300°

(b) This compound was methylated by boiling under reflux with dimethyl sulphate and potassium carbonate in 2-butanone. There was obtained the novel compound 7-bromo-3-hydroxymethyl-1-methyl-4-quinolone, m.p. >300° (from industrial methylated spirit).

(c) This compound was reacted with thionyl chloride in dichloromethane to give the novel compound 7-bromo-3-chloromethyl-1-methyl-4-quinolone hydrochloride.

(d) This compound was reacted with sodium methanethiolate in methanol to give a crude product which was purified by column chromatography over silica gel, eluting with dichloromethane:industrial methylated spirit 9:1 followed by column chromatography over silica gel, eluting with ethyl acetate. This gave the novel compound 7-bromo-1-methyl-3-methylthiomethyl-4-quinolone, m.p. 168°–170°.

(e) This sulphide was oxidised with an equimolar amount of 3-chloroperbenzoic acid to give the novel sulphoxide 7-bromo-1-methyl-3-methylsulphinylmethyl-4-quinolone, m.p. 204°–207° (from isopropanol).

(f) The sulphide from (d) was oxidised with 2 molar equivs. of 3-chloroperbenzoic acid to give the novel sulphone 7-bromo-1-methyl-3-methylsulphonylmethyl-4-quinolone, m.p. 243°–245° (from industrial methylated spirit).

EXAMPLE 23

In a similar way to that described in Example 10, the following reactions were carried out.

(a) 7-t-Butyl-4-hydroxyquinoline was reacted with formaldehyde in aqueous sodium hydroxide to give the novel compound 7-t-butyl-3-hydroxymethyl-4-hydroxyquinolome, m.p. >300°.

(b) This compound was methylated by boiling under reflux with dimethyl sulphate and potassium carbonate in 2-butanone. There was obtained the novel compound 7-t-butyl-3-hydroxymethyl-1-methyl-4-quinolone, m.p. 146°–149° (from toluene:petroleum ether (b.p. 60°–80°)).

(c) This compound was reacted with thionyl chloride to give the corresponding novel 3-chloromethyl compound. This compound was reacted with sodium methanethiolate in methanol to give a product which was purified by column chromatography on silica gel, eluting with ethyl acetate. There was obtained the novel compound 7-t-butyl-1-methyl-3-methylthiomethyl-4-quinolone, m.p. 114°–116°.

(d) This sulphide was oxidised with an equimolar amount of 3-chloroperbenzoic acid to give the novel sulphoxide 7-t-butyl-1-methyl-3-methylsulphinylmethyl-4-quinolone, m.p. 166°–168° (from ethyl acetate).

(e) The sulphide from (c) was oxidised with 2 molar equivs. of 3-chloroperbenzoic acid to give the novel sulphone 7-t-butyl-1-methyl-3-methylsulphonylmethyl-4-quinolone, m.p. 216°–218° (from ethyl acetate).

The starting material for preparation (a) was prepared as follows.

A mixture of 3-t-butylaniline (67.6 g.) and diethyl ethoxymethylenemalonate was heated on the steam bath for 3 hours, the ethanol formed being collected by distillation. The resulting yellow oil was dissolved in diphenyl ether (200 ml.) and added during 0.5 hour to stirred diphenyl ether (800 ml.) at 250°–260°, the ethanol formed being collected by distillation. The mixture was stirred at 250°–260° for 0.5 hour, then allowed to cool to room temperature and diluted with an equal volume of petroleum ether (b.p. 60°–80°). THe precipitate was collected by filtration to give the novel compound ethyl 7-t-butyl-4-hydroxyquinoline-3-carboxylate, m.p. 279°–281°.

This compound (92.0 g.) was boiled under reflux with aqueous potassium hydroxide solution (10% w/v; 900 ml.) for 3 hours. The mixture was cooled and acidified with concentrated hydrochloric acid. The precipitate was collected, washed with water and dried to give the novel compound 7-t-butyl-4-hydroxyquinoline-3-carboxylic acid, m.p. 271° (dec.).

This compound (75 g.) was decarboxylated by adding it to diphenyl ether (850 ml.) at 260° during 0.5 hour. After a further 1.0 hour at 260°, the mixture was cooled to room temperature and diluted with an equal volume of petroleum ether (b.p. 80°–100°). The precipitate was collected, dried and recrystallised from industrial methylated spirit:water to give the novel compound 7-t-butyl-4-hydroxyquinoline, m.p. 207°–209°.

EXAMPLE 24

Ethyl iodide (2.93 g.) was added to a stirred mixture of 4-hydroxy-3-methylsulphonylmethylquinoline (1.93 g.), anhydrous potassium carbonate (2.3 g.) and 2-butanone (80 ml.) The mixture was boiled under reflux for 24 hours and the solvent was evaporated. The mixture was diluted with water (200 ml.) and left overnight. The mixture was filtered and the filtrate evaporated to dryness to give a white solid. This was purified by high pressure liquid chromatography over silica gel using ethyl acetate:isopropanol 9:1 as the eluant at a flow rate of 200 ml. per minute. There was obtained the novel compound 1-ethyl-3-methylsulphonylmethyl-4-quinolone, m.p. 162°–164°.

EXAMPLE 25

(a) A mixture of 4-hydroxy-3-hydroxymethylquinoline (5.0 g.), anhydrous potassium carbonate (1.6 g.), propyl bromide (2.6 ml.) and 2-butanone (500 ml.) was stirred and boiled under reflux for 18 hours. Additional propyl bromide (2 ml.) was added and the mixture boiled under reflux for 23 hours. The solvent was evaporated and the residue treated with water (100 ml.) and basified with 5 N aqueous sodium hydroxide. The solution was extracted with dichloromethane (4×100 ml.). The extract was dried and evaporated to give an oil. This oil was triturated with petroleum ether:ethyl acetate:industrial methylated spirit 12:1:1 to give the novel compound 3-hydroxymethyl-1-propyl-4-quinolone, m.p. 88°–91°.

In a similar way to that described in Example 10, this compound was converted successively to the following novel compounds:

(b) 3-chloromethyl-1-propyl-4-quinolone, m.p. 125°–127°

(c) 3-methylthiomethyl-1-propyl-4-quinolone, isolated as an oil (d) 3-methylsulphonylmethyl-1-propyl-4-quinolone, m.p. 144°–146° (from industrial methylated spirit).

EXAMPLE 26

(a) 4-Chloro-3-chloromethylquinoline (14.2 g.) was added to a stirred suspension of sodium methanesulphinate (7.3 g.) in dimethylformamide (150 ml.) at room temperature. The mixture was stirred for 14 hours at room temperature, then for 0.5 hour at 95°–100°. The solvent was evaporated to half volume and water added to the residue. The resulting solid product was collected and dissolved in dichloromethane. The solution was dried, filtered from charcoal, and evaporated. The resulting solid was triturated with petroleum ether to give the novel compound 4-chloro-3-methylsulphonylmethylquinoline, m.p. 202°–204°.

(b) This compound (2.5 g.) was added to methanolic sodium methoxide (from sodium, 0.25 g. and methanol, 50 ml.) and the mixture boiled under reflux for 2 hours. Further sodium methoxide (from sodium 0.25 g. and methanol, 5 ml.) was added and the mixture was boiled under reflux for 4 hours. The mixture was allowed to cool overnight, then diluted with 100 ml. water. The solid residue was collected and dried to give the novel 4-methoxy-3-methylsulphonylmethylquinoline, m.p. 151°–154°.

(c) The above compound (1.0 g.) was heated in an oil bath at 160° (oil temperature) for 1 hour. After cooling to room temperature, the product was dissolved in boiling methanol. The hot solution was filtered with charcoal and allowed to cool. This gave the crystalline product 1-methyl-3-methylsulphonylmethyl-4-quinolone, m.p. 200°–201°.

EXAMPLE 27

(a) To a stirred solution of 4-chloro-3-methylsulphonylmethyl-4-quinoline (5.0 g.) in dichloromethane (300 ml.) was added dimethyl sulphate (12.54 g.). The solution was stirred at room temperature for 4 days and then evaporated to half volume. The resulting mixture was cooled at 0°–5° overnight and filtered to give the novel compound 4-chloro-1-methyl-3-methylsulphonylmethylquinolinium methyl sulphate, m.p. 194°–197° (dec.).

(b) This compound (1.0 g.) was dissolved in 10% aqueous sodium bicarbonate (75 ml.) and the solution kept at room temperature for 45 minutes. Isolation of the product by extraction with dichloromethane and recrystallisation from methanol gave 1-methyl-3-methylsulphonylmethyl-4-quinolone, m.p. 202°–204°.

EXAMPLE 28

To a solution of 3-acetoxymethyl-1-methyl-4-quinolone (0.8 g.) in acetone (15 ml.) was added a solution of sodium methanesulphinate (0.53 g.) in water (10 ml.). The mixture was boiled under reflux for 24 hours. Further sodium methanesulphinate (0.14 g.) was added and the mixture was boiled under reflux for 4 hours. Acetone was evaporated from the mixture, causing the separation of a white solid which was recrystallised from industrial methylated spirit to give 1-methyl-3-methylsulphonylmethyl-4-quinolone, m.p. 195°–197°.

EXAMPLE 29

3-Chloromethyl-1-methyl-4-quinolone hydrochloride (2.0 g.) was added portionwise during 1 minute to a stirred suspension of sodium methanesulphinate (5.0 g.) in anhydrous dimethylformamide (70 ml.) at room temperature. The mixture was stirred at this temperature for 16 hours, then evaporated to dryness. The residue was triturated with water (50 ml.), filtered, the filtrate basified with aqueous sodium hydroxide and then extracted with dichloromethane (2×50 ml.). The combined extracts were dried over anhydrous magnesium sulphate and evaporated to give the novel 1-methyl-3-methylsulphonylmethyl-4-quinolone, m.p. 201°–204° (from acetone).

EXAMPLE 30

(a) In a similar way to that described in Example 18, 4-hydroxyquinoline was reacted with 40% aqueous formaldehyde and methanethiol in the presence of triethylamine to give the novel 4-hydroxy-3-methylthiomethylquinoline, m.p. 196°–197° (from isopropanol).

(b) A solution of 3-chloroperbenzoic acid (85%, 3.92 g.) in dichloromethane (100 ml.) was added dropwise to a stirred suspension of 4-hydroxy-3-methylthiomethylquinoline (4.4 g.) in the same solvent (200 ml.) at 0°–5°. Diethyl ether (500 ml.) was added to the resulting solution and the precipitated novel 4-hydroxy-3-methylsulphinylmethylquinoline was collected and used without further purification.

(c) To a stirred solution of 4-hydroxy-3-methylsulphinylmethylquinoline (4.4 g.) and potassium hydroxide (1.68 g.) in water (20 ml.) at 0°–5° was added dimethyl sulphate (2.52 g.). The solution was stirred at room temperature for 30 minutes, then neutralised with 5 N aqueous hydrochloric acid. The resultant sticky solid was triturated with industrial methylated spirit to give a solid product. The product was purified by high pressure liquid chromatography over silica gel, eluting with isopropanol:dichloromethane 95:5 at a flow rate of 200 ml. per minute. This procedure gave the novel 1-methyl-3-methylsulphinylmethyl-4-quinolone, m.p. 94°–96°.

EXAMPLE 31

(a) A mixture of 4-hydroxyquinoline (2.9 g.), sodium methanesulphinate (8.16 g.), 40% aqueous formaldehyde (4.5 ml.) and water (70 ml.) was stirred at 95°–100° for 24 hours. More formaldehyde solution (5 ml.) was added and the mixture stirred at 95°–100° for a further 24 hours. The mixture was cooled and filtered to give the novel 4-hydroxy-3-methylsulphonylmethylquinoline, m.p. 280°–282° (from industrial methylated spirit:-water).

(b) Dimethyl sulphate (3.0 ml) was added to a stirred solution of 4-hydroxy-3-methylsulphonylmethylquinoline (1.9 g.) and potassium hydroxide (1.4 g.) in water (20 ml.) at 5°. The mixture was stirred at room temperature for 4 hours, then filtered to give the novel 1-methyl-3-methylsulphonylmethyl-4-quinolone, m.p. 204°–205° (from acetone).

EXAMPLE 32

In the preparation of capsules, a mixture of equal parts by weight of 1-methyl-3-methylsulphonylmethyl-4-quinolone and calcium phosphate is encapsulated in hard gelatin capsules, each capsule containing 10 mg. of active ingredient.

EXAMPLE 33

In the preparation of tablets, the following mixture is dry granulated and compressed in a tableting machine to give tablets containing 10 mg. of active ingredient.

|  | parts by weight |
|---|---|
| Active compound | 10 |
| Lactose | 5 |
| Calcium Phosphate | 5 |
| Maize starch | 5 |

EXAMPLE 34

In the preparation of capsules, a mixture of equal parts by weight of 7-chloro-1-methyl-3-methylsulphinylmethyl-4-quinolone and calcium phosphate is encapsulated in hard gelatin capsules, each capsule containing 10 mg. of active ingredient.

EXAMPLE 35

In the preparation of capsules, a mixture of equal parts by weight of 7-chloro-1-methyl-3-methylsulphonylmethyl-4-quinolone and calcium phosphate is encapsulated in hard gelatin capsules, each capsule containing 10 mg. of active ingredient.

EXAMPLE 36

Tablets are prepared from the following ingredients.

|  | parts by weight |
|---|---|
| Active compound | 10.0 |
| Lactose | 78.5 |
| Polyvinylpyrrolidone | 5.0 |
| Maize starch | 15.0 |
| Magnesium stearate | 1.5 |

The active compound, the lactose and some of the starch are mixed and granulated with a solution of the polyvinylpyrrolidone in ethanol. The granulate is mixed with the magnesium stearate and the rest of the starch and the mixture is compressed in a tableting machine to give tablets containing 10 mg. of active ingredient.

EXAMPLE 37

Tablets, each containing 10 mg. 7-ethyl-1-methyl-3-methylsulphonylmethyl-4-quinolone are prepared by the method of Example 36. The tablets are enteric coated in a conventional manner using a solution of 20% cellulose acetate phthalate and 3% diethyl phthalate in ethanol:dichloromethane 1:1.

EXAMPLE 38

In the preparation of suppositories, 15 parts by weight of active compound is incorporated in 1300 parts by weight of tri-glyceride suppository base and the mixture formed into suppositories each containing 15 mg. of active compound.

EXAMPLE 39

Tablets are prepared as described in Example 36 using one of the following quinolones as the active compound.

(a) 1-Methyl-3-methylsulphonylmethyl-4-quinolone.

(b) 7-Chloro-1-methyl-3-methylsulphonylmethyl-4-quinolone.

(c) 7-Fluoro-1-methyl-3-methylsulphonylmethyl-4-quinolone.

(d) 1,7-Dimethyl-3-methylsulphonylmethyl-4-quinolone.

What we claim is:

1. Compounds of the general formula

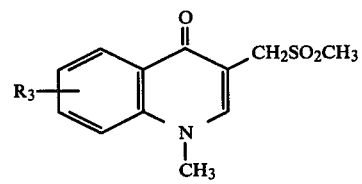

wherein $R_3$ is hydrogen, 7-chloro, 7-fluoro, 7-trifluoromethyl, 7-methyl or 6-fluoro.

2. Compounds of the general formula

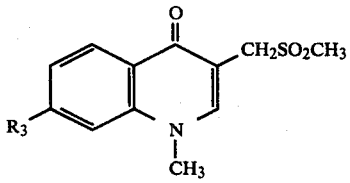

wherein $R_3$ is hydrogen, chloro, fluoro, trifluoromethyl, or methyl.

3. The compound of claim 2 wherein $R_3$ is hydrogen.
4. The compound of claim 2 wherein $R_3$ is chloro.
5. The compound of claim 2 wherein $R_3$ is fluoro.
6. The compound of claim 2 wherein $R_3$ is trifluoromethyl.
7. The compound of claim 2 wherein $R_3$ is methyl.
8. Therapeutic compositions which comprise a antihypertensive effective amount of a quinolone of the general formula

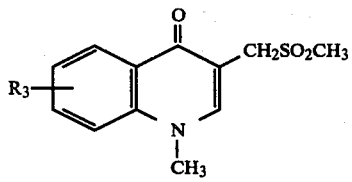

wherein $R_3$ is hydrogen, 7-chloro, 7-fluoro, 7-trifluoromethyl, 7-methyl or 6-fluoro, together with a pharmaceutically acceptable carrier.

9. A therapeutic composition as claimed in claim 8 in unit dosage form.
10. A therapeutic composition as claimed in claim 9 in the form of a tablet, capsule or suppository.
11. A therapeutic composition as claimed in claim 8 wherein $R_3$ is hydrogen.
12. A therapeutic composition as claimed in claim 8 wherein $R_3$ is 7-chloro.
13. A therapeutic composition as claimed in claim 8 wherein $R_3$ is 7-fluoro.
14. A therapeutic composition as claimed in claim 8 wherein $R_3$ is 7-methyl.
15. A therapeutic composition as claimed in claim 8 wherein $R_3$ is 7-trifluoromethyl.
16. A method of treating hypertension in a hypertensive mammal which comprises administering to the hypertensive mammal a therapeutically effective amount of a quinolone of the general formula

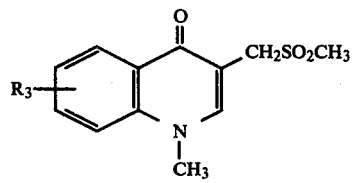

wherein $R_3$ is hydrogen, 7-chloro, 7-fluoro, 7-trifluoromethyl, 7-methyl or 6-fluoro.

17. A method as claimed in claim 16 wherein $R_3$ is hydrogen.
18. A method as claimed in claim 16 wherein $R_3$ is 7-chloro.
19. A method as claimed in claim 16 wherein $R_3$ is 7-fluoro.
20. A method as claimed in claim 16 wherein $R_3$ is 7-trifluoromethyl.
21. A method as claimed in claim 16 wherein $R_3$ is 7-methyl.
22. A therapeutic composition as claimed in claim 8, wherein $R_3$ is hydrogen, 7-chloro, 7-fluoro, 7-trifluoromethyl, or 7-methyl.
23. A method of treating hypertension as claimed in claim 8, wherein $R_3$ is hydrogen, 7-chloro, 7-fluoro, 7-trifluoromethyl, or 7-methyl.

* * * * *

UNITED STATES PATENT AND TRADEMARK OFFICE
CERTIFICATE OF CORRECTION

PATENT NO. : 4,447,435
DATED : May 8, 1984
INVENTOR(S) : Roy V. Davies

It is certified that error appears in the above—identified patent and that said Letters Patent is hereby corrected as shown below:

Col. 1, line 6; "quinoline" should read -- quinolone --
Col. 3, line 16; after "of" insert -- general --
Col. 4, line 38; "rats" should read -- tests --
Col. 5, approximately line 23 (heading of TABLE 1, third column);
" $R_3'$ " should read -- $R_3$ --

Col. 6, line 29; "hypertensive" should read -- hypertension --
Col. 6, line 61; "centrigrade" should read -- centigrade --
Col. 7, line 3; "The" should read -- This --
Col. 7, line 64; "solution" (first occurrence) should read
 -- sodium --
Col. 9, line 8; "60°-80°)." should read -- 60°-80°)). --
Col. 10, line 28; "soluttion" should read -- solution --
Col. 10, line 67; after "to" insert -- a --
Col. 16, line 67; "THe" should read -- The --

Signed and Sealed this

Second Day of April 1985

[SEAL]

Attest:

DONALD J. QUIGG

Attesting Officer    Acting Commissioner of Patents and Trademarks